(12) United States Patent
Okamoto et al.

(10) Patent No.: US 10,514,355 B2
(45) Date of Patent: Dec. 24, 2019

(54) GAS SENSOR

(71) Applicant: NGK INSULATORS, LTD., Nagoya-shi, Aichi (JP)

(72) Inventors: Taku Okamoto, Nagoya (JP); Noriko Hirata, Nagoya (JP); Yuki Nakayama, Nagoya (JP); Osamu Nakasone, Inabe (JP)

(73) Assignee: NGK INSULATORS, LTD., Nagoya (JP)

( * ) Notice: Subject to any disclaimer, the term of this patent is extended or adjusted under 35 U.S.C. 154(b) by 390 days.

(21) Appl. No.: 15/290,063

(22) Filed: Oct. 11, 2016

(65) Prior Publication Data

US 2017/0138894 A1     May 18, 2017

(30) Foreign Application Priority Data

Nov. 17, 2015    (JP) ................................ 2015-224642

(51) Int. Cl.
*G01N 27/407*     (2006.01)
*G01N 27/419*     (2006.01)

(52) U.S. Cl.
CPC ..... *G01N 27/4076* (2013.01); *G01N 27/4073* (2013.01); *G01N 27/4074* (2013.01); *G01N 27/4077* (2013.01); *G01N 27/419* (2013.01); *G01N 27/4071* (2013.01); *G01N 27/4075* (2013.01)

(58) Field of Classification Search
None
See application file for complete search history.

(56) References Cited

U.S. PATENT DOCUMENTS

| | | | |
|---|---|---|---|
| 6,136,170 | A * | 10/2000 | Inoue ................. G01N 27/4065 204/408 |
| 8,133,370 | B2 | 3/2012 | Roessler et al. |
| 8,366,893 | B2 | 2/2013 | Fujisaki et al. |

(Continued)

FOREIGN PATENT DOCUMENTS

| | | | |
|---|---|---|---|
| EP | 0859233 A2 * | 8/1998 | ........... G01N 27/407 |
| JP | 4405643 B2 | 1/2010 | |

(Continued)

*Primary Examiner* — Gurpreet Kaur
*Assistant Examiner* — Steven E Rosenwald
(74) *Attorney, Agent, or Firm* — Global IP Counselors, LLP

(57) ABSTRACT

A mixed-potential gas sensor for measuring a concentration of a predetermined gas component of a measurement gas includes sensing electrodes mainly made of an oxygen-ion conductive solid electrolyte and located on a surface of a sensor element, and at least one reference electrode including a cermet including Pt and an oxygen-ion conductive solid electrolyte. The sensing electrodes each include a cermet including a noble metal and an oxygen-ion conductive solid electrolyte. The noble metal includes Pt and Au. A Au abundance ratio, which is an area ratio of a portion covered with the Au to a portion at which the Pt is exposed in a surface of noble metal particles forming each of the sensing electrodes, differs among the sensing electrodes. The gas sensor determines a concentration of the predetermined gas component based on a potential difference between each of the sensing electrodes and the at least one reference electrode.

20 Claims, 9 Drawing Sheets

(56) References Cited

U.S. PATENT DOCUMENTS

| | | | | |
|---|---|---|---|---|
| 8,771,489 B2* | 7/2014 | Xiao | ............... | G01N 27/4045 |
| | | | | 204/430 |
| 2002/0092780 A1* | 7/2002 | Nadanami | .......... | G01N 27/4074 |
| | | | | 205/782 |
| 2003/0205078 A1* | 11/2003 | Hasei | ............... | G01N 27/4074 |
| | | | | 73/23.31 |
| 2005/0284759 A1* | 12/2005 | Kawase | ............ | G01N 27/4175 |
| | | | | 204/424 |
| 2010/0243447 A1* | 9/2010 | Fujisaki | ............ | G01N 27/4075 |
| | | | | 204/431 |
| 2012/0006692 A1* | 1/2012 | Liemersdorf | ........ | G01N 27/419 |
| | | | | 205/784 |
| 2014/0332379 A1* | 11/2014 | Nakasone | .............. | G01N 27/41 |
| | | | | 204/410 |

FOREIGN PATENT DOCUMENTS

| JP | 2011-058834 | * | 3/2011 | ............ G01N 27/41 |
|---|---|---|---|---|
| JP | 4914447 B2 | | 4/2012 | |
| JP | 5323752 B2 | | 10/2013 | |

\* cited by examiner

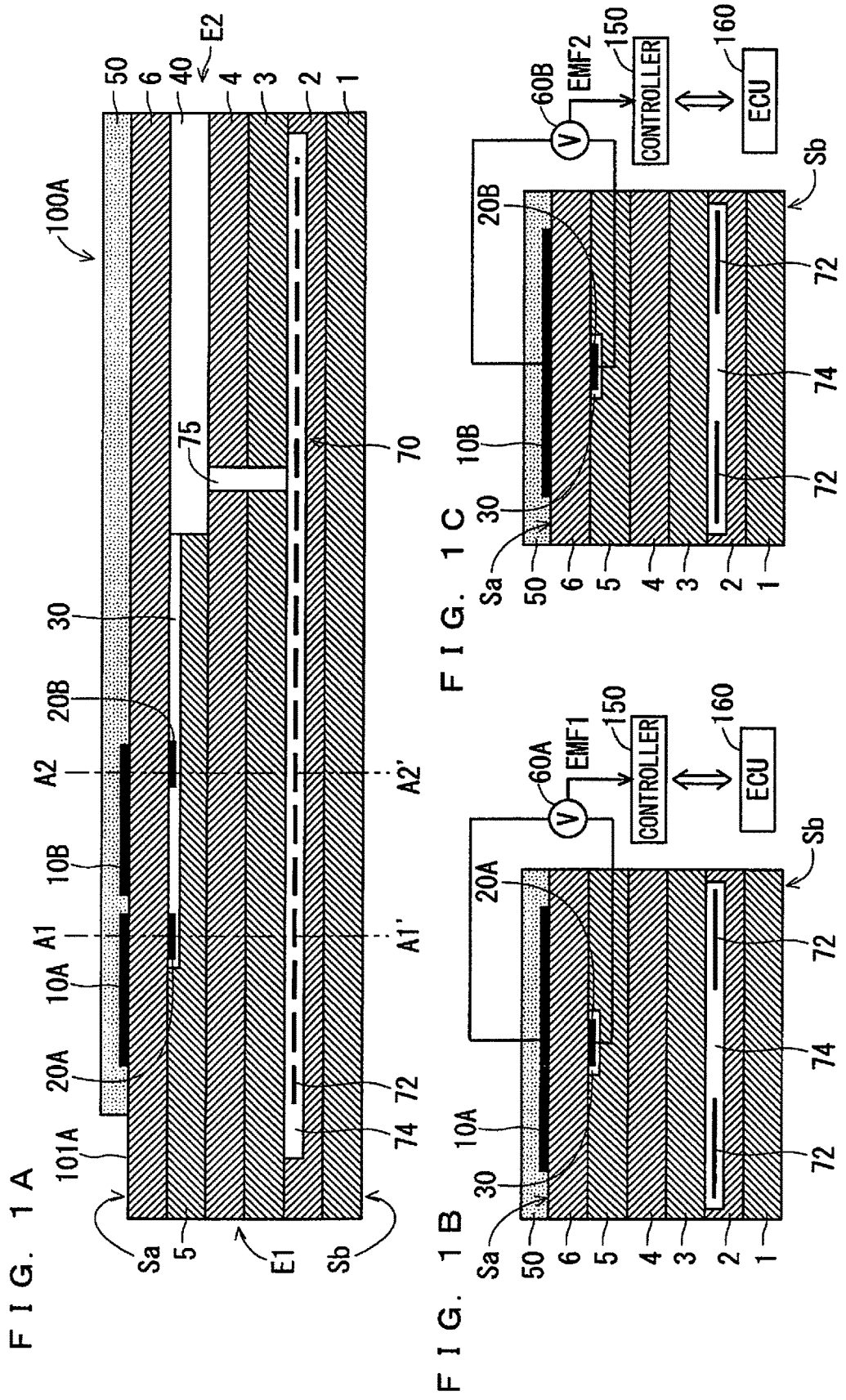

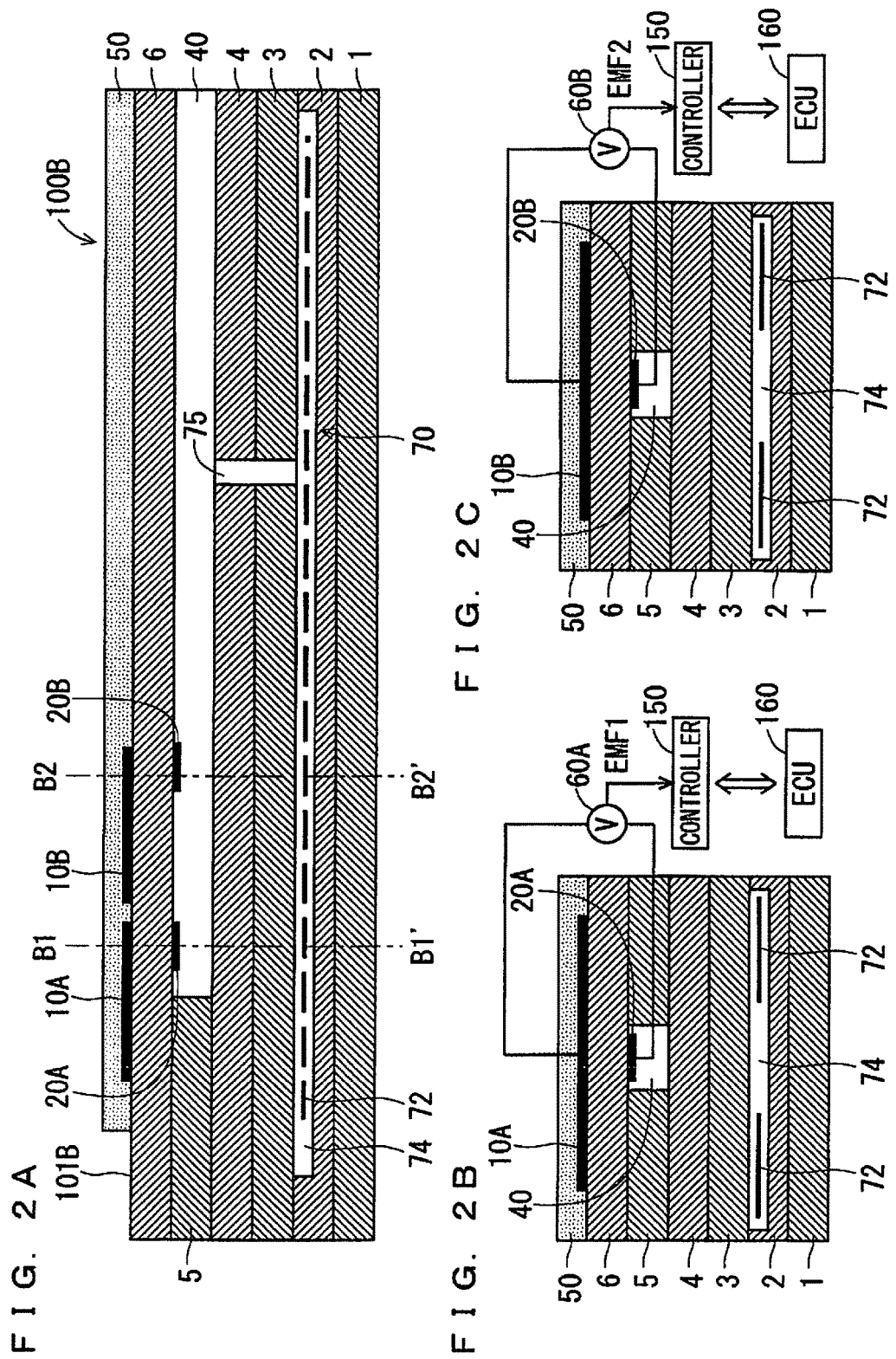

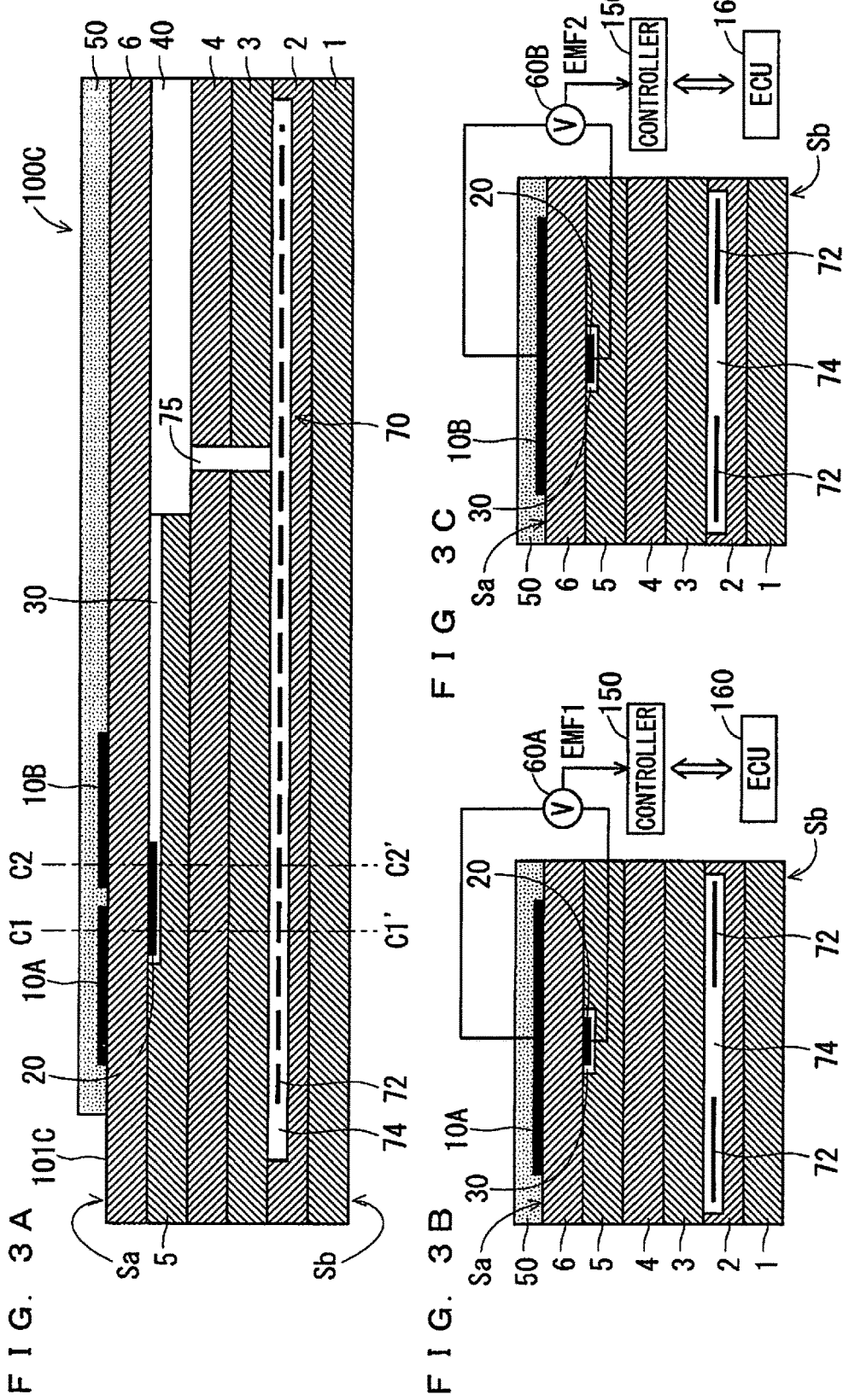

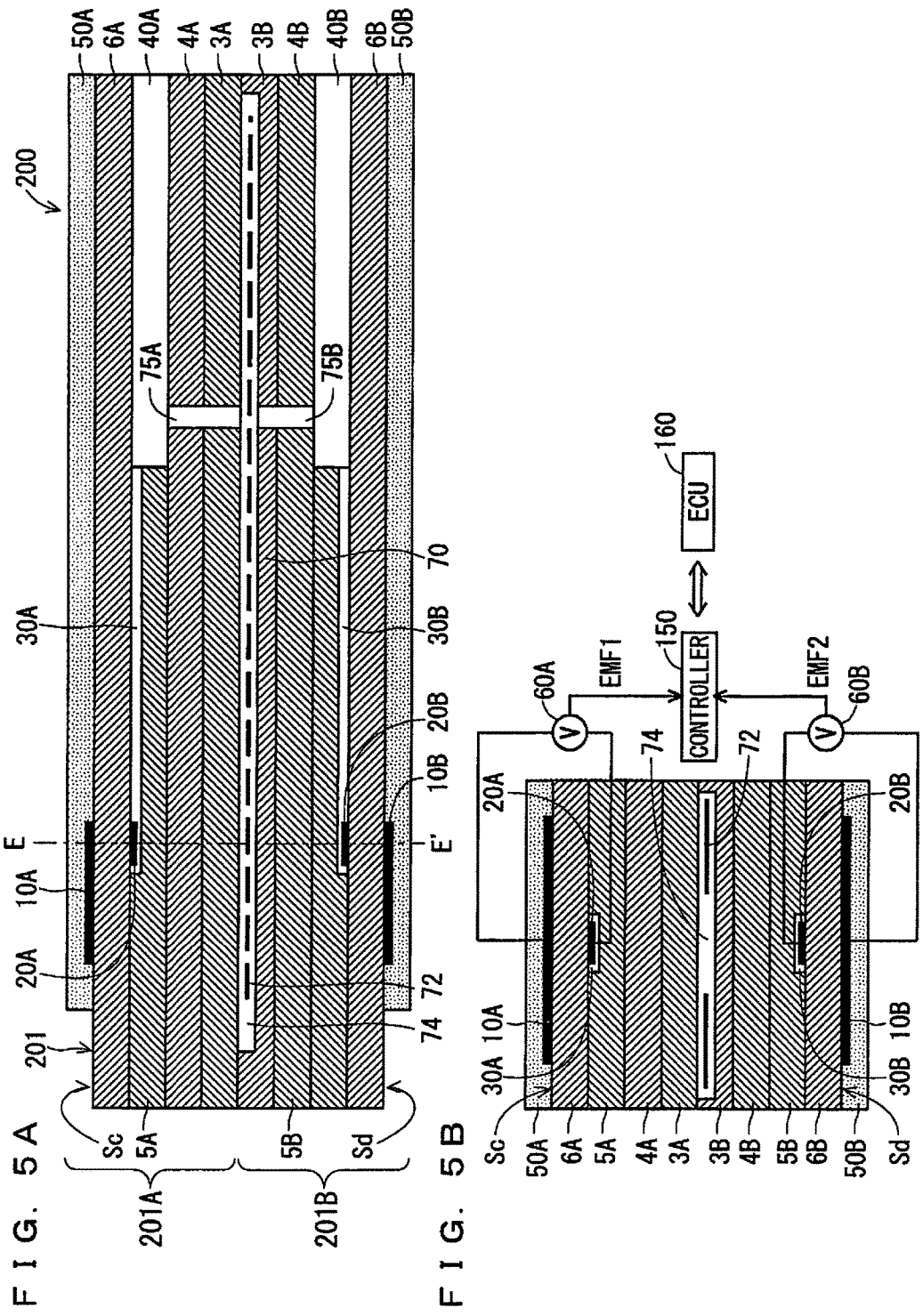

F I G . 7
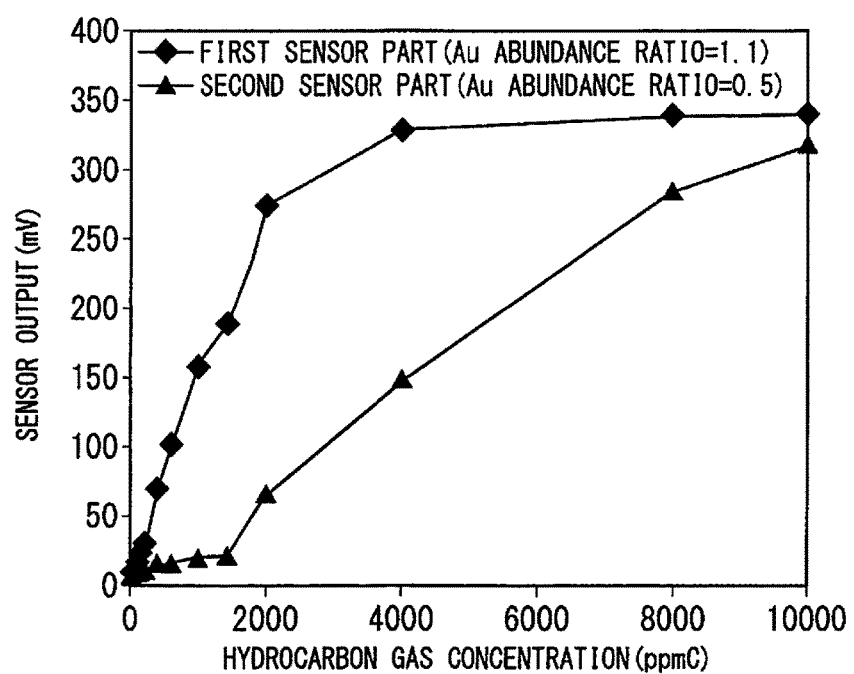

GAS SENSOR

BACKGROUND OF THE INVENTION

Field of the Invention

The present invention relates to a gas sensor for sensing a predetermined gas component of a measurement gas, and more particularly, to a sensing electrode of the gas sensor.

Description of the Background Art

Gas sensors that sense a predetermined gas component of a measurement gas to determine its concentration come in various types such as a semiconductor gas sensor, a catalytic combustion gas sensor, an oxygen-concentration difference sensing gas sensor, a limiting current gas sensor, and a mixed-potential gas sensor (for example, see Japanese Patent Nos. 4405643, 4914447, and 5323752). Some of these gas sensors are obtained by providing electrodes containing a noble metal as its main constituent to a sensor element mainly made of ceramic that is a solid electrolyte such as zirconia.

Japanese Patent No. 4405643 discloses a gas sensor provided with a thin layer mainly made of Pt or Au to compensate for the adhesion between a solid electrolyte and an electrode made of metal oxide and gold.

Japanese Patent No. 4914447 discloses a mixed-potential gas sensor including a first electrode formed through application of a Pt—Au paste and a second electrode formed through application of a Pt paste and Au plating.

Japanese Patent No. 5323752 discloses a limiting current gas sensor including a sensor element formed of solid electrolyte, which includes electrodes made of Pt—Au alloy as pumping electrodes.

In response to more stringent regulations on exhaust gas, there have recently been increasing demands for a diagnosis of failure in the performance of cleaning unburned hydrocarbon in an exhaust emission control system (TWC: three-way catalyst) of a gasoline engine and a diagnosis of failure in the performance of cleaning unburned hydrocarbon in an exhaust emission control system (DOC: diesel oxidation catalyst) of a diesel engine. These diagnoses require a gas sensor capable of sensing an unburned hydrocarbon gas and identifying its concentration.

The inventors of the present invention have made intensive studies to find out that in a sensing electrode made of Pt—Au alloy having an increased Au abundance ratio, a catalytic activity against a hydrocarbon gas is disabled, inducing a mixed potential having correlation with the concentration of the hydrocarbon gas. Such finding has led the inventors to a gas sensor capable of sensing a hydrocarbon gas with high sensitivity.

In the inventions disclosed in Japanese Patent Nos. 4405643 and 4914447, the concentration of a gas component is determined on the premise that both of the first electrode and the second electrode have a catalytic activity, although there may be a slight difference. In Japanese Patent No. 4914447, the relationship between the alloy composition of the electrode and the detection sensitivity is not clear.

Japanese Patent No. 5323752 discloses that a pumping electrode for a limiting current gas sensor is made of Pt—Au alloy such that a Au abundance ratio is 0.01 or more and 0.3 or less, thereby increasing the selective decomposition ability for oxygen in the pumping electrode. Japanese Patent No. 5323752 also discloses that a Au abundance ratio exceeding 0.3 is not preferable because such a ratio increases electrode impedance. Japanese Patent No. 5323752, however, discloses or suggests nothing about a mixed-potential gas sensor (needless to say, about its sensing electrode as well).

The concentration of a hydrocarbon gas of an exhaust gas discharged during a normal operation (during a steady operation) of a typical diesel engine is on the order of 2000 ppmC at most (ppmC represents parts per million of capacity ratio in terms of carbon, which holds true for the following). Therefore, it is also considered that such a gas sensor is sufficient that can measure the concentration of a hydrocarbon gas in the range of up to approximately 2000 ppmC.

However, when a fuel is sprayed intentionally for the process of regenerating a diesel particulate filter (DPF) or when an injector for fuel injection goes out of order, a hydrocarbon gas may be discharged at a concentration greatly exceeding 2000 ppmC, for example, 4000 ppmC or more. This leads to a need for a gas sensor capable of accurately measuring the concentration of a hydrocarbon gas also in such a high concentration range. Further, there is another need for measuring a wide concentration range from low to high concentrations by one gas sensor.

However, the measurement range of the concentration of a hydrocarbon gas by the gas sensor disclosed in Japanese Patent No. 4405643 is approximately 2000 ppmC at most, and such a gas sensor cannot meet the needs described above. Japanese Patent No. 4914447 merely discloses an example of measuring ammonia in the range of not more than 900 ppm and describes nothing about hydrocarbon, further, carbon monoxide.

SUMMARY OF THE INVENTION

The present invention relates to a gas sensor for sensing a predetermined gas component of a measurement gas, and more particularly, to a sensing electrode of the gas sensor.

According to the present invention, a mixed-potential gas sensor for measuring a concentration of a predetermined gas component of a measurement gas includes a sensor element mainly made of an oxygen-ion conductive solid electrolyte, a plurality of sensing electrodes located on a surface of the sensor element, and at least one reference electrode including a cermet including Pt and an oxygen-ion conductive solid electrolyte. The plurality of sensing electrodes each include a cermet including a noble metal and an oxygen-ion conductive solid electrolyte. The noble metal includes Pt and Au. A Au abundance ratio, which is an area ratio of a portion covered with the Au to a portion at which the Pt is exposed in a surface of noble metal particles forming each of the plurality of sensing electrodes, differs among the plurality of sensing electrodes. The gas sensor determines a concentration of the predetermined gas component based on a potential difference between each of the plurality of sensing electrodes and the at least one reference electrode.

The plurality of sensing electrodes are preferably a first sensing electrode and a second sensing electrode. The Au abundance ratio of the first sensing electrode is preferably 0.7 or more. The Au abundance ratio of the second sensing electrode is preferably 0.1 or more and less than 0.7. The gas sensor preferably determines the concentration of the predetermined gas component based on a first sensor output that is a potential difference between the first sensing electrode and the at least one reference electrode or a second sensor output that is a potential difference between the second sensing electrode and the at least one reference electrode.

According to the present invention, a gas sensor capable of measuring the concentration of an unburned hydrocarbon gas in a wide concentration range from low to high concentrations can be achieved.

The present invention therefore has an object to provide a gas sensor capable of accurately measuring a concentration of a target gas component in a concentration range larger than a conventional concentration range.

BRIEF DESCRIPTION OF THE DRAWINGS

FIGS. 1A, 1B, and 1C are sectional views schematically illustrating an example configuration of a gas sensor 100A according to a first configuration;

FIGS. 2A, 2B, and 2C are sectional views schematically illustrating an example configuration of a gas sensor 100B that is a modification of the gas sensor 100A;

FIGS. 3A, 3B, and 3C are sectional views schematically illustrating an example configuration of a gas sensor 100C according to a second configuration;

FIGS. 5A and 5B are sectional views schematically illustrating an example configuration of a gas sensor 200 according to a third configuration;

FIG. 7 is a graph illustrating first and second sensitivity characteristics of a gas sensor 100C including a first sensing electrode 10A whose Au abundance ratio is 1.1 and a second sensing electrode 10B whose Au abundance ratio is 0.5;

DESCRIPTION OF THE PREFERRED EMBODIMENTS

First Configuration

Figure 4A:
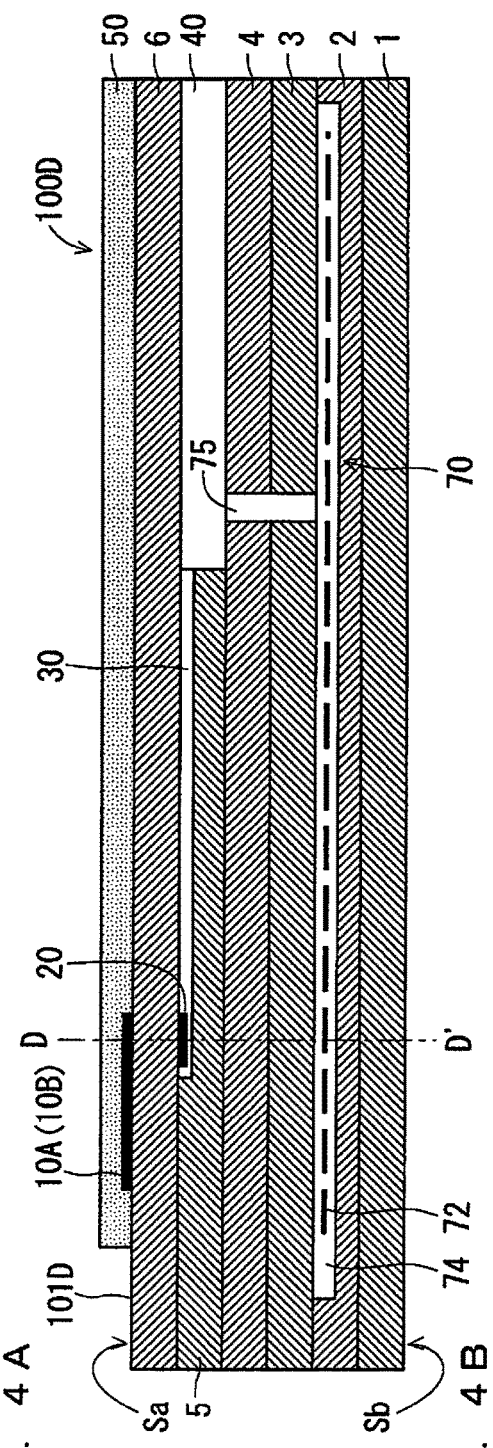
FIGS. 4A and 4B are sectional views schematically illustrating an example configuration of a gas sensor 100D that is a modification of the gas sensor 100C according to the second configuration.

FIGS. 1A, 1B, and 1C are schematic sectional views schematically illustrating an example configuration of a gas sensor 100A according to a first configuration of the present invention. FIG. 1A is a vertical sectional view of a sensor element 101A that is a main component of the gas sensor 100A, which is taken along the longitudinal direction of the sensor element 101A. FIG. 1B is a view including a cross-section of the sensor element 101A perpendicular to the longitudinal direction of the sensor element 101A at a position A1-A1' of FIG. 1A. FIG. 1C is a view including a cross-section of the sensor element 101A perpendicular to the longitudinal direction of the sensor element 101A at a position A2-A2' of FIG. 1A.

The gas sensor 100A according to the first configuration of the present invention is a so-called mixed-potential gas sensor. Generally speaking, the gas sensor 100A determines the concentration of the gas component of a measurement gas using potential differences that occur between a first sensing electrode 10A, which is provided on the surface of the sensor element 101A mainly made of ceramic being an oxygen-ion conductive solid electrolyte such as zirconia ($ZrO_2$), and a second reference electrode 20A, which is provided inside the sensor element 101A, and between a second sensing electrode 10B and a second reference electrode 20B, which are provided similarly to the electrodes above, due to a difference in the concentration of a gas component being a measurement target between the portions near the electrodes based on the principle of mixed potential.

More specifically, the gas sensor 100A preferably determines the concentration of a predetermined gas component of a measurement gas, where the measurement gas is an exhaust gas present in an exhaust pipe of an internal combustion engine such as a diesel engine or a gasoline engine. In this specification, description will be given of an example case where a predetermined gas component being a measurement target is an unburned hydrocarbon gas. In such a case, examples of the unburned hydrocarbon gas include carbon monoxide (CO) in addition to typical hydrocarbon gases (gases classified as hydrocarbons in terms of chemical formula) such as $C_2H_4$, $C_3H_6$, and n-C8. In the presence of a plurality of unburned hydrocarbon gases in a measurement gas, a potential difference occurring between the first sensing electrode 10A and the first reference electrode 20A and a potential difference occurring between the second sensing electrode 10B and the second reference electrode 20B have values reflecting all the plurality of unburned hydrocarbon gases, and thus, a concentration value to be determined is also a total sum of the concentrations of the plurality of unburned hydrocarbon gases.

The sensor element 101A mainly includes a reference gas introduction layer 30, a reference gas introduction space 40, and a surface protective layer 50 in addition to the first sensing electrode 10A, the second sensing electrode 10B, the first reference electrode 20A, and the second reference electrode 20B.

In the first configuration of the present invention, the sensor element 101A has the structure in which six layers, namely, a first solid electrolyte layer 1, a second solid electrolyte layer 2, a third solid electrolyte layer 3, a fourth solid electrolyte layer 4, a fifth solid electrolyte layer 5, and a sixth solid electrolyte layer 6, each formed of an oxygen-ion conductive solid electrolyte, are laminated in the stated order from the bottom side of FIGS. 1A, 1B, and 1C. The sensor element 101A additionally includes other components mainly between these layers or on an outer peripheral surface of the element. The solid electrolytes constituting these six layers are fully airtight. Such a sensor element 101A is manufactured by, for example, laminating ceramic green sheets corresponding to the individual layers, which have been subjected to a predetermined process and printing of a circuit pattern, and further, by integrating the laminated layers through firing.

The gas sensor 100A does not necessarily need to include the sensor element 101A formed of such a laminated body including the six layers. The sensor element 101A may be formed as a laminated body having more or fewer layers or may not have a laminated structure.

In the following description, for convenience' sake, the surface, which is located as the upper surface of the sixth solid electrolyte layer 6 in FIGS. 1A, 1B, and 1C, is referred to as a front surface Sa of the sensor element 101A, and the surface, which is located as the lower surface of the first solid electrolyte layer 1 in FIGS. 1A, 1B, and 1C, is referred to as a rear surface Sb of the sensor element 101A. In the determination of the concentration of the unburned hydrocarbon gas in a measurement gas with the gas sensor 100A, a predetermined range starting from a distal end E1 being one end of the sensor element 101A, which includes at least the first sensing electrode 10A and the second sensing electrode 10B, is disposed in a measurement gas atmosphere; the other portion including a base end E2 opposite to the distal end E1 is disposed so as not to be in contact with the measurement gas atmosphere.

The first sensing electrode 10A and the second sensing electrode 10B are electrodes for sensing a measurement gas. The first sensing electrode 10A and the second sensing electrode 10B are formed as porous cermet electrodes made of Pt containing a predetermined ratio of Au, namely, Pt—Au alloy and zirconia. The first sensing electrode 10A and the second sensing electrode 10B are provided at positions closer to the distal end E1 that is one end in the longitudinal direction of the sensor element 101A on the front surface Sa of the sensor element 101A so as to be adjacent to each other in the longitudinal direction. The first sensing electrode 10A and the second sensing electrode 10B are provided in a substantially rectangular shape in a plan view. The gas sensor 100A is placed such that, in its use, the sensor element 101A corresponding to at least the portion in which the first sensing electrode 10A and the second sensing electrode 10B are provided is exposed to a measurement gas.

The catalytic activities of the first sensing electrode 10A and the second sensing electrode 10B against an unburned hydrocarbon gas are disabled in their respective predetermined concentration ranges by preferably determining the composition of the Pt—Au alloy being their constituent material. That is, the decomposition reaction of an unburned hydrocarbon gas is inhibited in the first sensing electrode 10A and the second sensing electrode 10B. In the gas sensor 100A, accordingly, the potentials of the first sensing electrode 10A and the second sensing electrode 10B selectively vary with respect to (has correlation with) the unburned hydrocarbon gas, in accordance with their concentrations. In other words, the first sensing electrode 10A and the second sensing electrode 10B are provided in their respective concentration ranges so as to have high dependence of potential on concentration for an unburned hydrocarbon gas while having low dependence of potential on concentration for components of other measurement gas.

More specifically, the first sensing electrode 10A and the second sensing electrode 10B are provided so as to have different Au abundance ratios on the surface of the Pt—Au alloy particles constituting those electrodes, thereby exhibiting a remarkable dependence of potential on concentration in different concentration ranges. In this configuration, the first sensing electrode 10A and the second sensing electrode 10B are provided such that the first sensing electrode 10A exhibits a remarkable dependence of potential on concentration in a relatively low concentration range and that the second sensing electrode 10B exhibits a remarkable dependence of potential on concentration in a relatively high concentration range. Though described below in detail, this means that the first sensing electrode 10A is used to sense an unburned hydrocarbon gas in a lower concentration range and the second sensing electrode 10B is used to sense an unburned hydrocarbon gas in a higher concentration range.

In the following, unless otherwise specified, the configuration examples of the first sensing electrode 10A and the second sensing electrode 10B are as follows: the first sensing electrode 10A is formed with the Au abundance ratio of 1.1 so as to exhibit a remarkable dependence of potential on concentration in the concentration range of approximately 0 to 2000 ppmC, and the second sensing electrode 10B is formed with the Au abundance ratio of 0.5 so as to exhibit a remarkable dependence of potential on concentration in the concentration range of approximately 2000 to 10000 ppmC. The first sensing electrode 10A and the second sensing electrode 10B will be described below in detail.

In this specification, the Au abundance ratio means an area ratio of the portion covered with Au to the portion at which Pt is exposed in the surface of the noble metal particles constituting each of the first sensing electrode 10A and the second sensing electrode 10B. In this specification, a Au abundance ratio is calculated from a peak intensity of a peak detected for Au and Pt, obtained using X-ray photoelectron spectroscopy (XPS) by a relative sensitivity coefficient method. The Au abundance ratio is 1 when the area of the portion at which Pt is exposed is equal to the area of the portion covered with Au.

The first reference electrode 20A and the second reference electrode 20B are electrodes having a substantially rectangular shape in a plan view, which are provided inside the sensor element 101A and serve as a reference in the determination of the concentration of the measurement gas. The first reference electrode 20A and the second reference electrode 20B are provided as the porous cermet electrodes of Pt and zirconia.

It suffices that the first reference electrode 20A and the second reference electrode 20B have a porosity of 10% or more and 30% or lower and a thickness of 5 μm or more and 15 μm or less. The plane sizes of the first reference electrode 20A and the second reference electrode 20B may be smaller than those of the first sensing electrode 10A and the second sensing electrode 10B as illustrated in FIGS. 1A, 1B, and 1C or may be equal to those of the first sensing electrode 10A and the second sensing electrode 10B.

The reference gas introduction layer 30 is a layer made of porous alumina, which is provided inside the sensor element 101A to cover the first reference electrode 20A and the second reference electrode 20B. The reference gas introduction space 40 is an internal space provided near the base end E2 of the sensor element 101A. Air (oxygen), serving as a reference gas in the determination of the concentration of an unburned hydrocarbon gas, is externally introduced into the reference gas introduction space 40.

The reference gas introduction space 40 and the reference gas introduction layer 30 are in communication with each other, and accordingly, in the use of the gas sensor 100A, the surroundings of the first reference electrode 20A and the second reference electrode 20B are always filled with air (oxygen) through the reference gas introduction space 40 and the reference gas introduction layer 30. During the use of the gas sensor 100A, thus, the first reference electrode 20A and the second reference electrode 20B always have a constant potential.

The reference gas introduction space 40 and the reference gas introduction layer 30 are provided so as not to come into contact with a measurement gas owing to their surrounding solid electrolytes. This prevents the second reference electrode 20A and the second reference electrode 20B from coming into contact with the measurement gas even when the first sensing electrode 10A and the first sensing electrode 10B are exposed to the measurement gas.

In the case illustrated in FIGS. 1A, 1B, and 1C, the reference gas introduction space 40 is provided in such a manner that part of the fifth solid electrolyte layer 5 is in communication with the exterior on the base end E2 of the sensor element 101A. The reference gas introduction layer 30 is provided so as to extend in the longitudinal direction of the sensor element 101A between the fifth solid electrolyte layer 5 and the sixth solid electrolyte layer 6.

The surface protective layer 50 is a porous layer made of alumina, which is provided so as to cover at least the first sensing electrode 10A and the second sensing electrode 10B on the front surface Sa of the sensor element 101A. The surface protective layer 50 is provided as an electrode protective layer that prevents or reduces the degradation of the first sensing electrode 10A and the second sensing electrode 10B due to continuous exposure to a measurement gas during the use of the gas sensor 100A. In the case illustrated in FIGS. 1A, 1B, and 1C, the surface protective layer 50 is provided so as to cover not only the first sensing electrode 10A and the second sensing electrode 10B but also substantially the entire front surface Sa of the sensor element 101A except for a predetermined range starting from the distal end E1.

As illustrated in FIGS. 1B and 1C, the gas sensor 100A is equipped with a first potentiometer 60A capable of measuring a potential difference between the first sensing electrode 10A and the first reference electrode 20A and a second potentiometer 60B capable of measuring a potential difference between the second sensing electrode 10B and the second reference electrode 20B. Although FIGS. 1B and 1C schematically illustrate wiring of the first sensing electrode 10A, the first reference electrode 20A, and the first potentiometer 60A and wiring of the second sensing electrode 10B, the second reference electrode 20B, and the second potentiometer 60B, in an actual sensor element 101A, connection terminals (not shown) are provided correspondingly to the respective electrodes on the front surface Sa or the rear surface Sb on the base end E2 side, and wiring patterns (not shown), which connect the respective electrodes and their corresponding connection terminals, are formed on the front surface Sa and inside the element. The first sensing electrode 10A and the first reference electrode 20A are electrically connected with the first potentiometer 60A, and the second sensing electrode 10B and the second reference electrode 20B are electrically connected with the second potentiometer 60B via the wiring patterns and the connection terminals.

Hereinbelow, a potential difference between the first sensing electrode 10A and the first reference electrode 20A, which is measured by the first potentiometer 60A, is also referred to as a first sensor output or EMF1, and a potential difference between the second sensing electrode 10B and the second reference electrode 20B, which is measured by the second potentiometer 60B, is also referred to as a second sensor output or EMF2. In the sensor element 101A, the configuration for providing the first sensor output is generically called a first sensor part, and the configuration for providing the second sensor output is generically called a second sensor part.

The first sensor output and the second sensor output are both output to the controller 150 that controls the operation of the gas sensor 100A. The first sensor output and the second sensor output provided to the controller 150 are further provided to an electronic control unit (ECU) 160 that entirely controls the internal combustion engine. The electronic control unit (ECU) 160 then performs computations based on these outputs, thereby determining the concentration of the unburned hydrocarbon gas near the sensor element 101A. Although FIGS. 1B and 1C each individually illustrate the controller 150 and the ECU 160 for the sake of illustration, FIGS. 1B and 1C actually show the same controller 150 and the same ECU 160.

The sensor element 101A further includes a heater part 70 that performs temperature control of heating the sensor element 101A and maintaining the temperature of the sensor element 101A, to enhance the oxygen ion conductivity of the solid electrolyte. The heater part 70 includes a heater 72, a heater insulating layer 74, and a pressure diffusion hole 75.

The heater 72 is an electric resistor provided inside the sensor element 101A. The heater 72, which is connected with a heater electrode (not shown) being in contact with the rear surface Sb of the sensor element 101A (a lower surface of the first solid electrolyte layer 1 in FIGS. 1A, 1B, and 1C), generates heat by being fed power from the controller 150 via the heater electrode to heat the solid electrolytes forming the sensor element 101A and maintain their temperatures.

In the case illustrated in FIGS. 1A, 1B, and 1C, the heater 72 is buried while being vertically sandwiched between the second solid electrolyte layer 2 and the third solid electrolyte layer 3 so as to range from the base end E2 to the positions below the first sensing electrode 10A and the second sensing electrode 10B near the distal end E1. This enables the adjustment of the entire sensor element 101A to the temperature at which the solid electrolytes are activated.

The heater insulating layer 74 is an insulating layer formed of an insulator such as alumina on the upper and lower surfaces of the heater 72. The heater insulating layer 74 is formed for electrical insulation between the second solid electrolyte layer 2 and the heater 72 and for electrical insulation between the third solid electrolyte layer 3 and the heater 72.

The pressure diffusion hole 75 is a part provided to penetrate the third solid electrolyte layer 3 and the fourth solid electrolyte layer 4 to be in communication with the reference gas introduction space 40, which is formed to mitigate an internal pressure rise associated with a temperature rise in the heater insulating layer 74.

In the determination of the concentration of an unburned hydrocarbon gas in a measurement gas using the gas sensor 100A having such a configuration, as described above, the sensor element 101A in only a predetermined range, which starts from the distal end E1 and includes at least the first sensing electrode 10A and the second sensing electrode 10B, is disposed in a space containing a measurement gas, whereas the sensor element 101A on the base end E2 is apart from the space. And then, air (oxygen) is supplied to the reference gas introduction space 40. The heater 72 heats the sensor element 101A to an appropriate temperature from 400° C. to 800° C., preferably from 500° C. to 700° C., more preferably from 500° C. to 600° C.

In such a state, a potential difference occurs between the first sensing electrode 10A exposed to the measurement gas and the first reference electrode 20A disposed in the air and between the second sensing electrode 10B and the second reference electrode 20B that are disposed similarly to the electrodes above. As described above, however, the potentials of the first reference electrode 20A and the second reference electrode 20B disposed under the air (having a constant oxygen concentration) are maintained at constant potentials, whereas the potentials of the sensing electrode 10A and the second sensing electrode 10B each have a dependence on concentration for the unburned hydrocarbon gas of the measurement gas. Therefore, a certain functional relationship (referred to as sensitivity characteristics) holds between the concentration of the unburned hydrocarbon gas and the first sensor output and between the concentration of the unburned hydrocarbon gas and the second sensor output. The first sensing electrode 10A and the second sensing electrode 10B are provided in such a manner that respective concentration ranges in which the dependence of potential on concentration is remarkable differ from each other, so that the sensitivity characteristics of these two electrodes differ from each other.

In the following description, for example, the sensitivity characteristic for the first sensor output may be referred to as, for example, a first sensitivity characteristic.

In the actual determination of the concentration of an unburned hydrocarbon gas, in advance, a plurality of different mixed gases, each of which has a known concentration of an unburned hydrocarbon gas, are used as the measurement gas, and the first and second sensitivity characteristics are experimentally identified by measuring the first sensor output and the second sensor output of each measurement gas. The first and second sensitivity characteristics are then stored in the ECU 160.

The sensor element 101A provides two outputs, the first sensor output and the second sensor output, to the controller 150. The condition (output selection condition) for selecting only one of the two outputs to use the one output in the calculation of the concentration of an unburned hydrocarbon gas is also set in advance and stored in the ECU 160.

In the actual use of the gas sensor 100A, the ECU 160 calculates the concentration of an unburned hydrocarbon gas based on one of the values of the first and second sensor outputs selected in accordance with the preset output selection condition, which vary from moment to moment in accordance with the concentration of an unburned hydrocarbon gas in a measurement gas, and sensitivity characteristic corresponding to the one value. The concentration of an unburned hydrocarbon gas in a measurement gas can thus be determined almost in real time.

Modification of First Configuration

FIGS. 2A, 2B, and 2C are schematic sectional views schematically illustrating an example configuration of a gas sensor 100B that is a modification of the gas sensor 100A. FIG. 2A is a vertical sectional view of a sensor element 101B that is a main component of the gas sensor 100B, which is taken along the longitudinal direction of gas sensor 100B. FIG. 2B is a view including a cross-section of the sensor element 101B perpendicular to the longitudinal direction of the sensor element 101B at a position B1-B1' of FIG. 2A. FIG. 2C is a view including a cross-section of the sensor element 101B perpendicular to the longitudinal direction of the sensor element 101B at a position B2-B2' of FIG. 2A.

The gas sensor 100B is provided in such a manner that the reference gas introduction space 40 of the sensor element 101A of the gas sensor 100A is extended up to below the first sensing electrode 10A, whereas the reference gas introduction layer 30 is omitted and the first reference electrode 20A and the second reference electrode 20B are exposed to the reference gas introduction space 40. The other configurational elements are similar to those of the gas sensor 100A. A first sensor output and a second sensor output are respectively generated in the first sensor part and the second sensor part as in the case of the gas sensor 100A. In other words, the gas sensor 100B is also a so-called mixed-potential gas sensor similarly to the gas sensor 100A.

Accordingly, the gas sensor 100B having the configuration described above is also provided in such a manner that the first sensing electrode 10A and the second sensing electrode 10B exhibit a remarkable dependence of potential on concentration in different concentration ranges, as in the case of the gas sensor 100A. Therefore, the concentration of the unburned hydrocarbon gas in a measurement gas can be determined by disposing the sensor element 101B in the space containing the measurement gas in the manner described above after identifying the first and second sensitivity characteristics and determining output selection conditions.

Second Configuration

FIGS. 3A, 3B, and 3C are schematic sectional views schematically illustrating a configuration example of a gas sensor 100C according to a second configuration of the present invention. FIG. 3A is a vertical sectional view of a sensor element 101C that is a main component of the gas sensor 100C, which is taken along the longitudinal direction of the sensor element 101C. FIG. 3B is a view including a cross-section of the sensor element 101C perpendicular to the longitudinal direction of the sensor element 101C at a position C1-C1' of FIG. 3A. FIG. 3C is a view including a cross-section of the sensor element 101C perpendicular to the longitudinal direction of the sensor element 101C at a position C2-C2' of FIG. 3A.

The gas sensor 100C is also a so-called mixed-potential gas sensor similarly to the gas sensors 100A and 100B. However, the sensor element 101C of the gas sensor 100C includes only one reference electrode 20 for the first sensing electrode 10A and the second sensing electrode 10B, differently from the sensor element 101A and the sensor element 101B in which the first reference electrode 20A and the second reference electrode 20B are respectively provided correspondingly to the first sensing electrode 10A and the second sensing electrode 10B. In other words, the sensor element 101C is configured such that the first and second sensor parts share the reference electrode 20.

The other configurational elements are similar to those of the gas sensors 100A and 100B.

In the case of the sensor element 101C, as illustrated in FIGS. 3B and 3C, a potential difference between the first sensing electrode 10A and the reference electrode 20 is measured by the first potentiometer 60A as a first sensor output, and a potential difference between the second sensing electrode 10B and the reference electrode 20 is measured by the second potentiometer 60B as a second sensor output.

Accordingly, the gas sensor 100C having the configuration described above is also provided in such a manner that the first sensing electrode 10A and the second sensing electrode 10B exhibits a remarkable dependence of potential on concentration in different concentration ranges, as in the cases of the gas sensor 100A and the gas sensor 100B. Therefore, the concentration of the unburned hydrocarbon gas in a measurement gas can be determined by disposing the sensor element 101C in the space containing a measurement gas in the manner described above after identifying the first and second sensitivity characteristic and determining output selection conditions.

Although the reference electrode 20 illustrated in FIGS. 3A, 3B, and 3C has a plane size larger than the plane sizes of the first reference electrode 20A and the second reference electrode 20B illustrated in FIGS. 1A, 1B, and 1C, the reference electrode 20 may have a plane size as large as the plane sizes of the first reference electrode 20A and the second reference electrode 20B.

Modification of Second Configuration

Figure 4B:
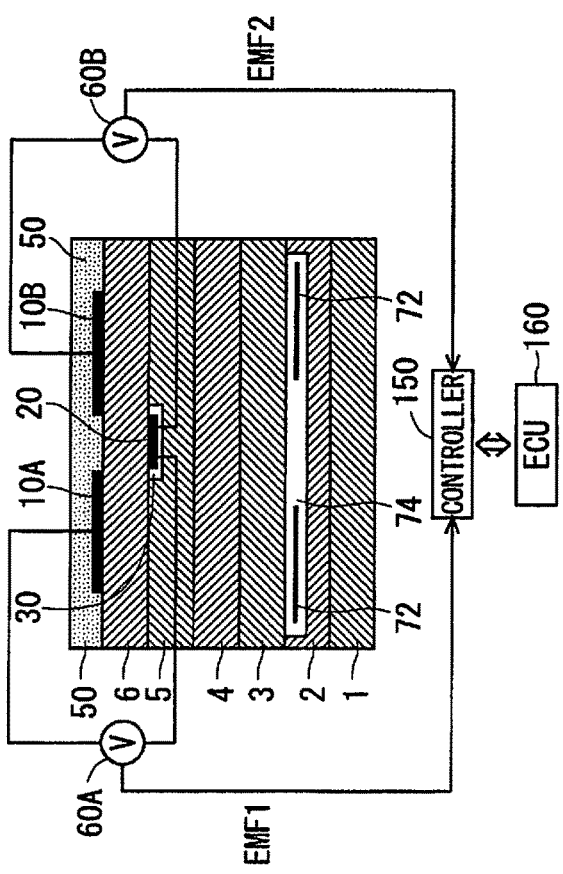

FIGS. 4A and 4B are schematic sectional views schematically illustrating a configuration example of a gas sensor 100D that is a modification of the gas sensor 100C. FIG. 4A is a vertical sectional view of the sensor element 101D that is a main component of the gas sensor 100D, which is taken along the longitudinal direction of the sensor element 101D. FIG. 4B is a view including a cross-section of the sensor element 101D perpendicular to the longitudinal direction of the sensor element 101D at a position D-D' of FIG. 4A.

The gas sensor 100D is also a so-called mixed-potential gas sensor similarly to the gas sensors 100A to 100C. Besides, the sensor element 101D of the gas sensor 100D has a configuration in which the first and second sensor parts share the reference electrode 20 similarly to the sensor element 101C. The sensor element 101D differs from the sensor element 101C in that the sensor element 101D includes the first sensing electrode 10A and the second sensing electrode 10B provided adjacent to each other in the element width direction as illustrated in FIG. 4B, since the sensor element 101C includes the first sensing electrode 10A and the second sensing electrode 10B provided adjacent to each other in its longitudinal direction. The other configurational elements are similar to those of the gas sensors 100A to 100C.

Also in the case of the sensor element 101D, as illustrated in FIG. 4B, a potential difference between the first sensing electrode 10A and the reference electrode 20 is measured by the first potentiometer 60A as a first sensor output, and a potential difference between the second sensing electrode 10B and the reference electrode 20 is measured by the second potentiometer 60B as a second sensor output.

Accordingly, the gas sensor 100D having the configuration described above is also provided in such a manner that the first sensing electrode 10A and the second sensing electrode 10B exhibit a remarkable dependence of potential on concentration in different concentration ranges, as in the cases of the gas sensors 100A to 100C. Therefore, the concentration of an unburned hydrocarbon gas in a measurement gas can be measured by disposing the sensor element 101D in the space containing a measurement gas in the manner described above after identifying the first and second sensitivity characteristic and determining output selection conditions.

Third Configuration

FIGS. 5A and 5B are schematic sectional views schematically illustrating a configuration example of a gas sensor 200 according to a third configuration of the present invention. FIG. 5A is a vertical sectional view of a sensor element 201 that is a main component of the gas sensor 200, which is taken along the longitudinal direction of the sensor element 201. FIG. 5B is a view including a cross-section of the sensor element 201 perpendicular to the longitudinal direction of the sensor element 201 at a position E-E' of FIG. 5A.

Although the gas sensor 200 is a so-called mixed-potential gas sensor similarly to the gas sensors 100A to 100D, the configuration of the sensor element 201 greatly differs from the configurations of the sensor elements 101A to 101D.

Generally speaking, the sensor element 201 is configured such that its upper and lower portions are substantially symmetrical with respect to the heater part 70 provided at almost the center in the element thickness direction. Hereinbelow, the portion of the sensor element 201, which is above the heater part 70 in FIGS. 5A and 5B, is referred to as an upper element portion 201A, and the portion of the sensor element 201, which is under the heater part 70 in FIGS. 5A and 5B, is referred to as a lower element portion 201B. Note that the terms "upper" and "lower" are merely used in relation to FIGS. 5A and 5B and do not mean that the vertical relationship is maintained in the actual use of the sensor element 201.

The layer structures of the upper element portion 201A and the lower element portion 201B are substantially the same as the structure from the third solid electrolyte layer 3 to the surface protective layer 50 of the sensor element 101 of the gas sensor 100A according to the first configuration illustrated in FIGS. 1A, 1B, and 1C.

Specifically, in the upper element portion 201A, a third solid electrolyte layer 3A to a sixth solid electrolyte layer 6A respectively corresponding to the third solid electrolyte layer 3 to the sixth solid electrolyte layer 6 of the sensor element 101 are laminated in order on the heater part 70, and a reference gas introduction layer 30A, a reference gas introduction space 40A, and a surface protective layer 50A respectively corresponding to the reference gas introduction layer 30, the reference gas introduction space 40, and the surface protective layer 50 are provided at positions similar to those of the sensor element 101. In the lower element portion 201B, similarly, a third solid electrolyte layer 3B to a sixth solid electrolyte layer 6B respectively corresponding to the third solid electrolyte layer 3 to the sixth solid electrolyte layer 6 of the sensor element 101 are laminated in order on the heater part 70, and a reference gas introduction layer 30B, a reference gas introduction space 40B, and a surface protective layer 50B are provided at positions similar to those of the sensor element 101.

However, the sensor element 200, which includes the upper element portion 201A and the lower element portion 201B, differs from the sensor element 101 in the arrangement of electrodes. The upper element portion 201A includes a single first sensing electrode 10A on the surface (referred to as a front surface Sc of the sensor element 201), which is located as the upper surface of the sixth solid electrolyte layer 6A in FIGS. 5A and 5B, and a single first reference electrode 20A between the fifth solid electrolyte layer 5A and the sixth solid electrolyte layer 6A in a manner of being covered with the reference gas introduction layer 30A. The lower element portion 201B includes a single first sensing electrode 10B on the surface (referred to as a rear surface Sd of the sensor element 201), which is located as the upper surface of the sixth solid electrolyte layer 6B in FIGS. 5A and 5B, and a single second reference electrode 20B between the fifth solid electrolyte layer 5B and the sixth solid electrolyte layer 6B in a manner of being covered with the reference gas introduction layer 30B. When viewed as a whole, the sensor element 201 includes a group of the first sensing electrode 10A and the first reference electrode 20A and a group of the second sensing electrode 10B and the second reference electrode 20B similarly to the sensor element 101A. Also, the sensor element 201 includes the first sensing electrode 10A and the second sensing electrode 10B provided so as to exhibit a remarkable dependence of potential on concentration in different concentration ranges similarly to the sensor elements 101A to 101D.

Accordingly, the gas sensor 201 having the configuration described above can also determine the concentration of an unburned hydrocarbon gas in a measurement gas by disposing the sensor element 201 in the space containing a measurement gas in the manner described above after identifying the first and second sensitivity characteristics and determining output selection conditions, as in the cases of the gas sensors 100A to 100D.

Details of Sensing Electrode

As described above, in the gas sensors 100A to 100D and 200, the first sensing electrode 10A and the second sensing electrode 10B are formed so as to disable the catalytic activity against an unburned hydrocarbon gas in the respective concentration ranges. This is achieved by adding gold (Au) in addition to platinum (Pt) that is a main component to the first sensing electrode 10A and the second sensing electrode 10B as their conductive components (noble metal components).

As the Au abundance ratio becomes higher, Au tends to become thicker on the surface of the noble metal particles forming a sensing electrode. More specifically, a Au-rich Pt—Au alloy tends to be formed near the surface of Pt-rich Pt—Au alloy particles. As such a tendency becomes more conspicuous, the catalytic activity in a sensing electrode is more likely to be disabled.

Figure 6:
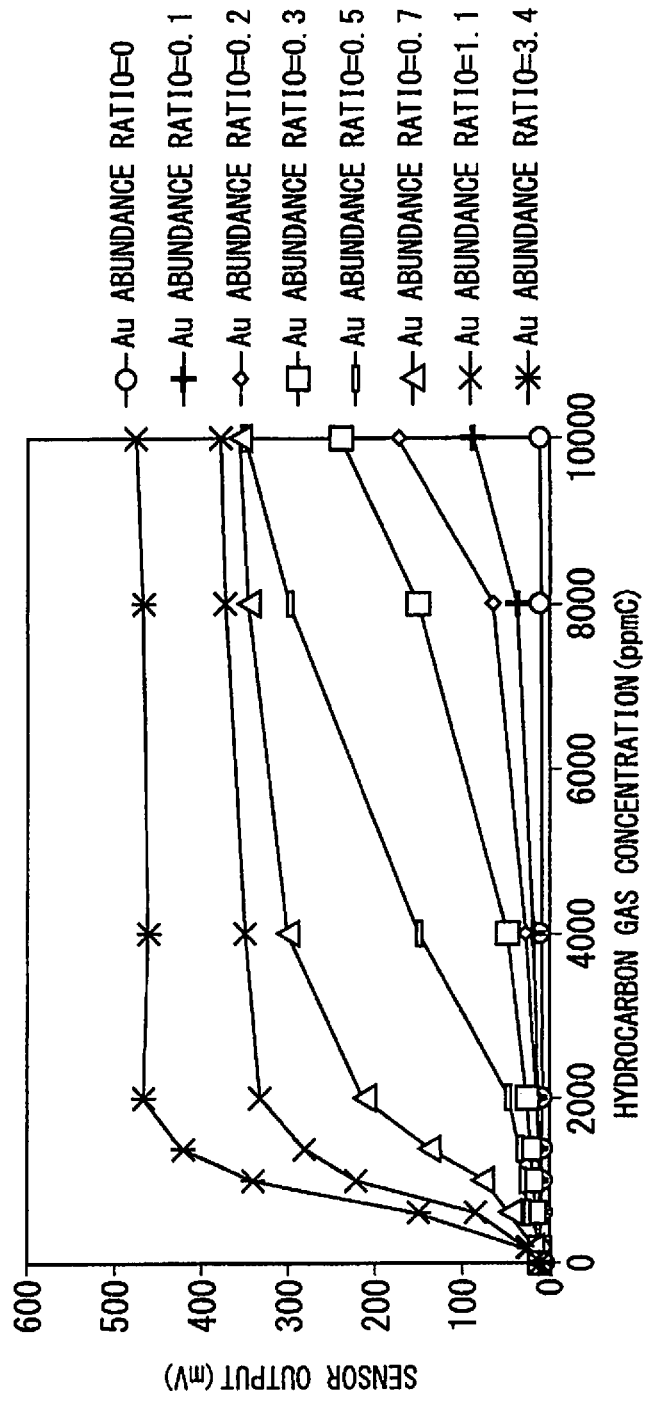
FIG. 6 is a graph illustrating sensitivity characteristics of eight types of sensor elements each including a sensing electrode and a reference electrode and having a different Au abundance ratio in the sensing electrode.

FIG. 6 is a graph illustrating the sensitivity characteristics (changes in sensor output with respect to the concentration of a hydrocarbon gas) in eight types of sensor elements each including one sensing electrode and one reference electrode and having a different Au abundance ratio in the sensing electrode. The configuration of the sensor element substantially corresponds to the configuration of the sensor element 101A excluding the second sensing electrode 10B and the second reference electrode 20B.

The measurement conditions for sensor output and the analysis conditions for Au abundance ratio when such sensitivity characteristics are obtained are as follows.
Measurement Conditions for Sensor Output
  Element Control Temperature: 600° C.
  Gas Atmosphere: $O_2$=10%, $H_2O$=5%, $C_2H_4$=200–10000 ppmC
  Gas Flow Rate: 5 L/min
  Pressure: 1 atm
  Electrode Protective Layer: Porosity of 40%, 12 μm
  Analysis Conditions for Au Abundance Ratio
  Analyzer: X-ray Photoelectron Spectrometer (AXIS-HS from Simadzu/KRATOS Co.)
  X-ray Source: Monochromatic Al
  Tube Voltage, Tube Current: 15 kV, 15 mA
  Lens Condition: Magnetic (analysis area of 120 um in diameter)
  Resolution: Pass Energy 80
  Scanning Rate: 200 eV/min (step of 1 eV)

FIG. 6 shows that in the case where the Au abundance ratio in the sensing electrode is zero (i.e., in the case where the metal component in the sensing electrode is Pt alone), the graph levels off, that is, no sensor output is obtained even at a high concentration of a hydrocarbon gas.

But, as the Au abundance ratio becomes higher from 0.1 to 0.2 to 0.3 to 0.5, the graph begins to slope gradually from the higher concentration side. An almost linear relationship is observed in the range of not less than 4000 ppmC for a Au abundance ratio of 0.3 and in the range of not less than 2000 ppmC for a Au abundance ratio of 0.5.

However, as the Au abundance ratio further becomes higher from 0.5 to 0.7 to 1.1 to 3.4, a sensor output is more likely to become saturated on the higher concentration side while the slope of the graph tends to become steeper on the lower concentration side. Specifically, for a Au abundance ratio of 0.7, although the graph slopes steeply in the range of not more than 4000 ppmC, the graph slopes gently in the range of not less than 4000 ppmC and levels off in the range exceeding 8000 ppmC. For Au abundance ratios of 1.1 and 3.4, although the slope of the graph is steep in the range of not more than 2000 ppm, the sensor output becomes almost saturated in the range of not less than 2000 ppmC.

From the viewpoint of providing adequate measurement accuracy, it is empirically considered that the sensor output desirably changes with a rate of a minimum of 50 mV per 2000 ppmC. From the viewpoint of measuring a trace amount of unburned hydrocarbon gas with a higher sensitivity, larger changes in sensor output on the lower concentration side are preferable. In view of the above, if a sensing electrode capable of sensing a trace amount of unburned hydrocarbon gas with high accuracy is selected based on the data of FIG. 6, it is judged that the use of the sensing electrode whose Au abundance ratio is 0.7 or more is appropriate. FIG. 6, however, shows that such a sensing electrode has difficulty in providing measurement accuracy in the range exceeding 4000 ppmC even for a Au abundance ratio of 0.7.

In the case of the sensing electrode whose Au abundance ratio is 0.5, the sensor output value levels off at a value of almost zero in the range of not more than 2000 ppmC, but changes in sensor output per 2000 ppmC exceed 50 mV at least up to 10000 ppmC in the range of not less than 2000 ppmC. This indicates that, in the case of using such a sensing electrode, the concentration of an unburned hydrocarbon gas can preferably be obtained from the sensor output in the range of not less than 2000 ppmC.

FIG. 6 also reveals that the concentration of an unburned hydrocarbon gas can be obtained preferably from a sensor output value in the range of at least 4000 to 10000 ppmC if the Au abundance ratio in the sensing electrode is 0.3, and in the range of at least 8000 to 10000 ppmC if the Au abundance ratio is 0.1 or more and 0.2 or less. In the range of 8000 to 10000 ppmC, the slope of a graph tends to be steep for Au abundance ratios of 0.2 and 0.3.

Formed to include both of the first sensing electrode 10A and the second sensing electrode 10B whose sensitivity characteristics differ from each other due to different Au abundance ratios, in consideration of such a relationship between the Au abundance ratio of the sensing electrode and the sensitivity characteristics of the gas sensor, are the gas sensors 100A to 100D and 200. Specifically, the sensing electrode for use in a lower concentration range is formed so as to provide a Au abundance ratio of 0.1 or more and less than 0.7 and the sensing electrode for use in the range of a high concentration range is formed so as to provide a Au abundance ratio of 0.7 or more, to thereby achieve a measurable concentration range larger than that of a mixed-potential gas sensor including a single sensing electrode. In other words, each of the gas sensors 100A to 100D and 200 can measure the concentration of an unburned hydrocarbon gas targeted for a wide concentration range from low to high concentrations, which cannot be measured by conventional gas sensors.

For example, in the case where the first sensing electrode 10A is formed to have a Au abundance ratio of 1.1 and the second sensing electrode 10B is formed to have a Au abundance ratio of 0.5 as in the configuration example above, the former has excellent sensitivity characteristics in the concentration range of 0 to 2000 ppmC, and the latter has excellent sensitivity characteristics in the concentration range of 2000 to 10000 ppmC. As a whole, the gas sensor can thus determine the concentration of an unburned hydrocarbon gas in the range of 0 to 10000 ppmC.

The combination of Au abundance ratios of two sensing electrodes is not limited to the above. For example, the first sensing electrode 10A may be formed to have a Au abundance ratio of 0.7, and the second sensing electrode 10B may be formed to have a Au abundance ratio of 0.3. In such a case, the former has excellent sensitivity characteristics in the concentration range of 0 to 4000 ppmC, and the latter has excellent sensitivity characteristics in the concentration range of 4000 to 10000 ppmC. As a whole, also, the gas sensor can determine the concentration of an unburned hydrocarbon gas in the range of 0 to 10000 ppmC. Alternatively, other combinations may be employed in cases including the case not illustrated in FIG. 6.

The conceivable reason why the dependence of sensor output on concentration becomes remarkable on the higher concentration side in the case where the Au abundance ratio is small and the dependence of sensor output on concentration becomes remarkable on the lower concentration side in the case where the Au abundance ratio is large as illustrated in FIG. 6 is as follows: in the former case, unburned hydrocarbon of an exhaust gas burns due to the Pt catalytic activity before the unburned hydrocarbon reaches a three-phase interface to cause an electrochemical reaction, because of a high concentration of Pt present in the surface of Pt—Au alloy particles, whereas in the latter case, part of the unburned hydrocarbon of the exhaust gas does not burn but reaches the three-phase interface in the form of an unburned hydrocarbon, thus causing an electrochemical reaction to produce a potential.

How the sensitivity characteristics vary with respect to the Au abundance ratios illustrated in FIG. 6 relates to a sensor element including one sensing electrode and one reference electrode. Also, it is empirically confirmed that the first sensor output and the second sensor output of the gas sensor including two sensing electrodes and two reference electrodes, such as the sensor elements 101A to 101D and 201, has a similar tendency.

It suffices that the volume ratio between a noble metal component and zirconia of the first sensing electrode 10A and the second sensing electrode 10B is approximately from 4:6 to 8:2.

For the gas sensors 100A to 100D and 200 to preferably exhibit their functions, the porosities of the first sensing electrode 10A and the second sensing electrode 10B are preferably 10% or more and 30% or less, and the thicknesses of the first sensing electrode 10A and the second sensing electrode 10B are preferably 5 μm or more.

The plane sizes of the first sensing electrode 10A and the second sensing electrode 10B may be appropriately determined, and it suffices that, for example, the length in the longitudinal direction of the sensor element is approximately 2 to 10 mm and the length in the direction perpendicular to the longitudinal direction is approximately 1 to 5 mm.

Setting of Output Selection Conditions

As described above, the gas sensors 100A to 100D and 200 each include two sensing electrodes, and accordingly, the sensor elements 101A to 101D and 201 constantly output two outputs, a first sensor output and a second sensor output. However, the first sensor part and the second sensor part have different sensitivity characteristics, and thus, if it is assumed that the concentration of an unburned hydrocarbon gas is constant near the element (if variations in concentration between the positions at which the two sensing electrodes are disposed are neglected), only one of the first and second sensor outputs usually corresponds to the concentration of the unburned hydrocarbon gas near the element.

To accurately determine the concentration of an unburned hydrocarbon gas using the gas sensors 100A to 100D and 200, thus, the conditions for output (output selection conditions) need to be determined in advance as to any of the first and second sensor outputs, which vary from moment to moment, is selected to calculate a concentration. Such output selection conditions can be determined in three ways below. Any one of them may be selected appropriately in accordance with, for example, the way of using a gas sensor or the sensitivity characteristics of the gas sensor.

First Way: Selection based on How Internal Combustion Engine is Operated

In the first way, while the internal combustion engine that is an emission source of a measurement gas is in a normal operation, the ECU 160 instructs the controller 150 to provide only the first sensor output to the ECU 160, and in response to this instruction, the controller 150 provides only the first sensor output to the ECU 160. The ECU 160 then calculates the concentration of an unburned hydrocarbon gas based on the first sensitivity characteristic.

At the occurrence of a predetermined event in which the concentration of an unburned hydrocarbon gas in an exhaust gas is higher than that during the normal operation, such as the DPF regeneration process, the ECU 160 instructs the controller 150 to provide only the second sensor output to the ECU 160, and in response to this instruction, the controller 150 provides only the second sensor output to the ECU 160. The ECU 160 then calculates the concentration of an unburned hydrocarbon gas based on the second sensitivity characteristic.

When the internal combustion engine returns to the normal operation after the event, the ECU 160 again instructs the controller 150 to provide only the first sensor output to the ECU 160.

Such a way is based on the premise that during the normal operation of the internal combustion engine, a measurement gas does not contain an unburned hydrocarbon gas at a concentration exceeding the concentration range measurable by the first sensor part (in the configuration example above, 2000 ppmC or less).

Second Way: Selection according to Changes in Output

In the second way, the controller 150 constantly provides both of the first and second sensor outputs to the ECU 160. The ECU 160 differentiates the first and second sensor outputs with respect to time to calculate differential values. Letting the time differential value of the first sensor output be d(EMF1)/dt and the time differential value of the second sensor output be d(EMF2)/dt, the ECU 160 compares the magnitudes of |d(EMF1)/dt| and |d(EMF2)/dt| that are the absolute values of these values and calculates the concentration of an unburned hydrocarbon gas based on the value of the first sensor output and the first sensitivity characteristic if |d(EMF1)/dt|≥|d(EMF2)/dt|, or calculates the concentration of an unburned hydrocarbon gas based on the value of the second sensor output and the second sensitivity characteristic if |d(EMF1)/dt|<|d(EMF2)/dt|. The calculation may be performed in reverse if an equal sign is placed.

When the controller 150 samples the first sensor output and the second sensor output at predetermined sampling intervals Δt (for example, 100 msec), as an approximate process, the controller 150 may subsequently calculate a difference value ΔEMF1 of two sampling values successively sampled for the first sensor output and a difference value ΔEMF2 of two sampling values successively sampled for the second sensor output, and compare the magnitudes of absolute values |ΔEMF1/Δt| and |ΔEMF2/Δt| of values respectively obtained by dividing the difference values ΔEMF1 and ΔEMF2 by Δt. Then, the controller 150 may calculate the concentration of an unburned hydrocarbon gas based on the value of the first sensor output and the first sensitivity characteristic if |ΔEMF1/Δt|≥|ΔEMF2/Δt| or calculate the concentration of an unburned hydrocarbon gas based on the value of the second sensor output and the second sensitivity characteristic if |ΔEMF1/Δt|<|ΔEMF2/Δt|. Also in this case, the calculation may be performed in reverse if an equal sign is placed.

Such a way is based on the premise that the output from a sensor part whose measurement target range is the actual concentration of an unburned hydrocarbon gas is more likely to vary in real time.

Third Way: Selection based on Sensitivity Characteristics

In the third way, a threshold for the first sensor output or the second sensor output in use of the sensor output to calculate a concentration is set based on the first and second sensitivity characteristics identified before the use of a gas sensor (for example, at shipment) and is stored in the ECU 160 in advance together with the sensitivity characteristics. More specifically, an upper limit value (upper limit usable value) for the first sensor output or the lower limit value (lower limit usable value) for the second sensor output is determined.

In the actual use of the gas sensor, the controller 150 constantly provides both of the first and second sensor outputs to the ECU 160.

Then, in the case where the upper limit usable value for the first sensor output has been determined, the ECU 160 calculates the concentration of a hydrocarbon gas based on the first sensor output and the first sensitivity characteristic if the first sensor output provided from the controller 150 is not greater than the set upper limit usable value, and calculates the concentration of a hydrocarbon gas based on the second sensor output and the second sensitivity characteristic if the first sensor output exceeds the upper limit usable value.

In the case where the lower limit usable value for the second sensor output has been determined, the ECU 160 calculates the concentration of a hydrocarbon gas based on the second sensor output and the second sensitivity characteristic if the second sensor output provided from the controller 150 is not smaller than the set lower limit usable value, and calculates the concentration of a hydrocarbon gas based on the first sensor output and the first sensitivity characteristic if the second sensor output falls below the lower limit usable value.

FIG. 7 is a graph illustrating first and second sensitivity characteristics of the gas sensor 100C including the first sensing electrode 10A and the second sensing electrode 10B that satisfy the configuration example described above, which is illustrated to describe the third way. Here, the Au abundance ratio of the first sensing electrode 10A is 1.1 for the former characteristic, and the Au abundance ratio of the second sensing electrode 10B is 0.5 for the latter characteristic. The measurement conditions for the sensor output in the case where the sensitivity characteristics illustrated in FIG. 7 are obtained are the same as the conditions in the case where the sensitivity characteristics illustrated in FIG. 6 are obtained.

As illustrated in FIG. 7, the sensor output of the first sensor part is saturated at approximately 350 mV, and accordingly, an output value of not smaller than 350 mV cannot be obtained from the first sensor part. However, variations in sensor output value are small around 350 mV, and accordingly, directly employing the value of 350 mV as the upper limit usable value is not appropriate. Therefore, it is preferable to set 280 mV, which is a value of 80% of 350 mV, as the upper limit usable value.

In such a case, if the first sensor output from the first sensor part is not greater than 280 mV, the first sensor output and the first sensitivity characteristic are used to calculate the concentration of an unburned hydrocarbon gas. If the first sensor output exceeds 280 mV, the second sensor output and the second sensitivity characteristic at that time are used to calculate the concentration of an unburned hydrocarbon gas. The range of the concentration of a hydrocarbon gas in which the first sensor output exceeds 280 mV is over approximately 2000 ppmC. In the case of FIG. 7, however, the second sensor output in such a range has sufficient dependence on concentration, and thus, the concentration of an unburned hydrocarbon gas can preferably be obtained in this range.

Such a way is based on the premise that the concentration of an unburned hydrocarbon gas can be accurately calculated by selecting the value of a sensor output used to calculate the concentration of an unburned hydrocarbon gas based on actual sensitivity characteristics.

Process of Manufacturing Sensor Element

Next, the process of manufacturing the sensor elements 101A to 101D and 201 will be described using an example case where the sensor elements have the layer structures as illustrated in FIGS. 1A to 5B. Generally speaking, the sensor elements 101A to 101D and 201 illustrated in FIGS. 1A to 5B are each manufactured by forming a laminated body formed of green sheets containing an oxygen-ion conductive solid electrolyte such as zirconia as a ceramic component and by cutting and firing the laminated body. The oxygen-ion conductive solid electrolyte may be, for example, yttrium partially stabilized zirconia (YSZ).

Figure 8:
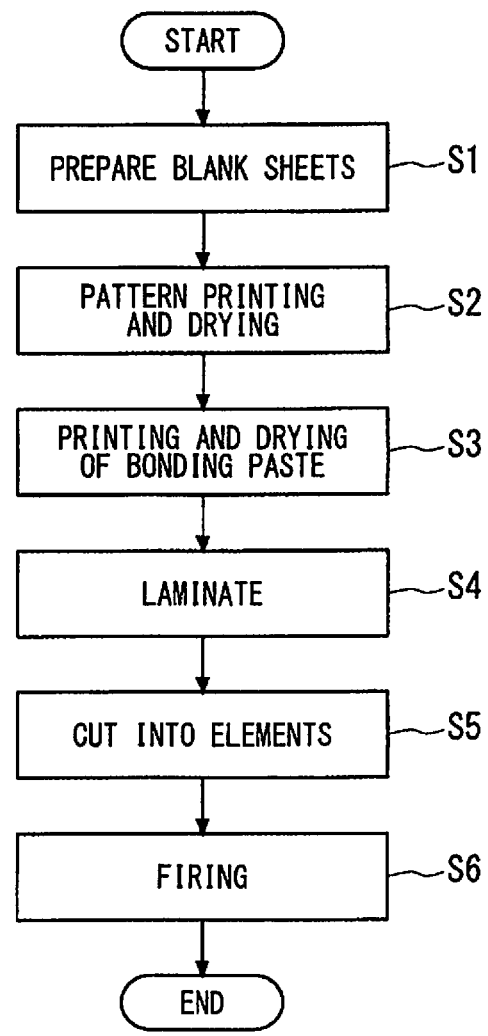
FIG. 8 is a flowchart illustrating a process of manufacturing the sensor elements 101A to 101D and 201.

FIG. 8 is a flowchart illustrating the process of manufacturing the sensor elements 101A to 101D and 201. In the manufacture of the sensor elements 101A to 101D and 201, first, blank sheets (not shown) that are green sheets having no pattern formed thereon are prepared (step S1). Specifically, six blank sheets corresponding to the first to sixth solid electrolyte layers 1 to 6 are prepared in the manufacture of the sensor elements 101A to 101D, and eight blank sheets corresponding to the third to sixth solid electrolyte layers 3A to 6A of the upper element portion 201A and the third to sixth solid electrolyte layers 3B to 6B of the lower element portion 201B are prepared in the manufacture of the sensor element 201. A blank sheet for forming the surface protective layer 50 (or the surface protective layers 50A and 50B) is prepared as well. A plurality of sheets holes used for positioning in printing and lamination are provided in the blank sheets. Such sheet holes are formed in advance through, for example, punching by a punching machine. For a green sheet whose corresponding layer forms an internal space, a penetration corresponding to the internal space is also provided in advance through, for example, punching as described above. All the blank sheets corresponding to the respective layers of the sensor elements 101A to 101D and 201 need not to have the same thickness.

After the preparation of the blank sheets corresponding to the respective layers, pattern printing and drying for forming various patterns are performed on the individual blank sheets (step S2). Specifically, electrode patterns of, for example, the first sensing electrode 10A, the second sensing electrode 10B, the first reference electrode 20A, and the first reference electrode 20B (or the first sensing electrode 10A, the second sensing electrode 10B, and the reference electrode 20), the reference gas introduction layer 30 (or the reference gas introduction layers 30A and 30B), internal wiring (not shown), and the like are formed.

Each pattern is printed by applying a paste for pattern formation, prepared in accordance with the characteristic required for each formation target, to the blank sheet by a known screen printing technique. Any known drying means is available for drying after printing.

The sensor elements 101A to 101D and 201 are characterized by the manner of preparing a conductive paste used to form the first sensing electrode 10A and the second sensing electrode 10B, which will be described below in detail.

After the pattern printing, printing and drying of a bonding paste are performed to laminate and bond the green sheets corresponding to the respective layers (step S3). Any known screen printing technique is available for printing of a bonding paste, and any known drying means is available for drying after printing.

Subsequently, crimping is performed in which the green sheets applied with an adhesive are laminated in a predetermined order, and the laminated green sheets are crimped on predetermined temperature and pressure conditions, to thereby form a laminated body (step S4). Specifically, green sheets that are lamination targets are laminated while being positioned at the sheet holes to be held in a predetermined lamination jig (not shown), and the green sheets together with the lamination jig are heated and pressurized by a lamination machine such as a known hydraulic pressing machine. The pressure, temperature, and time for heating and pressurizing depend on a lamination machine to be used, whose conditions may be set appropriately for good lamination.

After the laminated body is obtained as described above, subsequently, a plurality of parts of the laminated body are cut out as individual units (referred to as element bodies) of the sensor elements 101A to 101D and 201 (step S5). The cut out element bodies are fired under predetermined conditions, thereby producing the sensor elements 101A to 101D and 201 as described above (step S6). In other words, the sensor elements 101A to 101D and 201 are produced by integrally firing the solid electrolyte layers and the electrodes. The firing temperature is preferably 1200° C. or higher and 1500° C. or lower (for example, 1400° C.). The integral firing performed in such a manner provides satisfactory adhesion strength to the electrodes of the sensor elements 101A to 101D and 201.

The resultant sensor elements 101A to 101D and 201 are housed in a predetermined housing and incorporated into main bodies (not shown) of the gas sensors 100A to 100D and 200.

Conductive Paste for Forming Sensing Electrode

Next, a conductive paste used to form the first sensing electrode 10A and the second sensing electrode 10B will be described. The conductive paste for forming a sensing electrode is produced by using a Au ion-containing liquid as a Au starting material and mixing the Au ion-containing liquid with powdered Pt, powdered zirconia, and a binder. Any binder, which can disperse any other row material to the printable extent and vanishes through firing, may be appropriately selected. The production of a conductive paste in such a manner is referred to as liquid-state Au mixing.

Here, the Au ion-containing liquid is obtained by dissolving a salt containing Au ion or an organometallic complex containing Au ion in a solvent. The Au ion-containing salt may be, for example, tetrachloroauric(III) acid ($HAuCl_4$), sodium chloroaurate(III) ($NaAuCl_4$), or potassium dicyanoaurate(I) ($KAu(CN)_2$). The Au ion-containing organometallic complex may be, for example, gold(III) diethylenediamine trichloride ($[Au(en)_2]Cl_3$), gold(III) dichloro(1,10-phenanthroline)chloride ($[Au(phen)Cl_2]Cl$), dimethyl (trifluoroacetylacetonate)gold, or dimethyl (hexafluoroacetylacetonate)gold. Tetrachloroauric(III) acid or gold(III) diethylenediamine chloride ($[Au(en)_2]Cl_3$) is preferably used from the viewpoint of no impurity such as Na or K remaining in the electrode, easy handling, or dissolvability in the solvent. The solvent may be acetone, acetonitrile, or formamide as well as alcohols such as methanol, ethanol, and propanol.

Mixing can be performed by well-known means such as instillation. Although the obtained conductive paste contains Au present in ionic (complex ionic) state, the first sensing electrode 10A and the second sensing electrode 10B formed in the sensor elements 101A to 101C and 201 obtained through the above-mentioned manufacturing process contain Au mainly as an elemental metal or as an alloy with Pt.

Figure 9:
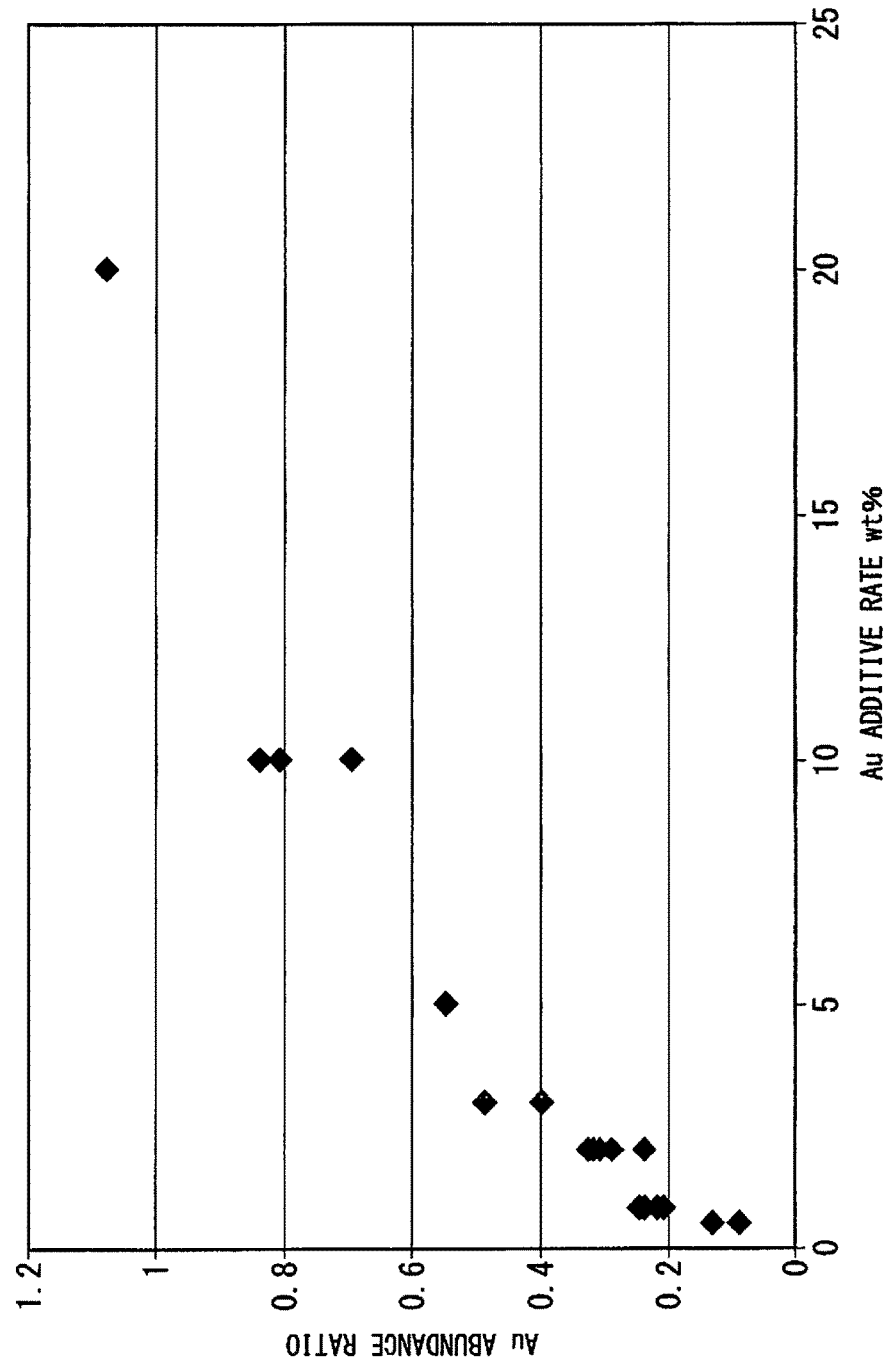
FIG. 9 illustrates Au abundance ratios in a sensing electrode 10 made of a conductive paste for the formation of a sensing electrode, which are plotted against Au additive rates, where the conductive paste is produced through liquid-state Au mixing.

FIG. 9 illustrates Au abundance ratios in a sensing electrode formed of a conductive paste for forming a sensing electrode, which are plotted against Au weight ratios (hereinbelow, referred to as Au additive rates) with respect to the weight of all the noble metal elements (a total weight of Pt and Au) of starting raw materials, where the conductive paste is produced through liquid-state Au mixing.

FIG. 9 reveals that a Au abundance ratio tends to increase with a Au additive rate monotonously, that a sensing electrode whose Au abundance ratio is 0.7 or more can be manufactured in the case where a Au additive rate is 10 wt % or more, and that a sensing electrode whose Au abundance ratio is 0.1 or more and less than 0.7 can be manufactured in the case where a Au additive rate is 0.5 wt % or more and less than 10 wt %. In other words, the use of a conductive paste whose Au additive rate is 10 wt % or more preferably forms the first sensing electrode 10A whose Au abundance ratio is 0.7 or more. The use of a conductive paste whose Au additive rate is 0.5 wt % or more and less than 10 wt % preferably forms the second sensing electrode 10B whose Au abundance ratio is 0.1 or more and less than 0.7.

Another Way of Producing Conductive Paste

In the production of a conductive paste for forming a sensing electrode, the conductive paste may be produced by using coated powders, which are obtained by coating powered Pt with Au, as starting raw materials, instead of producing the conductive paste through liquid-state Au mixing as described above. In such a case, a conductive paste for a sensing electrode is produced by mixing the coated powders, powdered zirconia, and a binder. Here, the coated powder used in the above production may be obtained by covering the particle surface of powered Pt with a Au film or applying Au particles to Pt powder particles.

Also in this case, the sensing electrode 10A and the second sensing electrode 10B can preferably be formed in accordance with a Au abundance ratio.

Modifications

In the embodiments above, a Au abundance ratio is determined based on the result of the XPS analysis. Alternatively, a sensing electrode may be subjected to auger electron spectroscopy (AES) analysis to determine a Au abundance ratio based on the result of the analysis. In such a case, an indicator of the Au abundance ratio on the surface of noble metal particles constituting a sensing electrode may be an index value that is substantially equivalent to the Au abundance ratio on the surface of the sensing electrode used in the embodiments or may be an index value convertible into the Au abundance ratio. In auger electron spectroscopy analysis, a Au abundance ratio may be determined where the broken surface of a sensor element is an analysis target.

In the sensor element 101D illustrated in FIGS. 4A and 4B, the first sensing electrode 10A and the second sensing electrode 10B are provided adjacent to each other in the element width direction, whereas a single reference electrode 20 is provided. Alternatively, the first reference electrode 20A and the second reference electrode 20B may be provided adjacent to each other correspondingly to the first sensing electrode 10A and the second sensing electrode 10B, respectively, in the element width direction.

Although the embodiments above have described the cases in which the measurement gas is an exhaust gas present in an exhaust pipe of an internal combustion engine such as a diesel engine or a gasoline engine and the concentration of an unburned hydrocarbon gas in the measurement gas is determined, the measurement targets of the gas sensors 100A to 100D and 200 are not limited to a hydrocarbon gas. The gas sensors 100A to 100D and 200 can also measure the concentrations of $NH_3$ and NOx based on the principle of mixed potential as in the embodiments above.

In the embodiments above, two sensing electrodes having different Au abundance ratios are provided, one of which is used for a lower concentration range and the other of which is used for a higher concentration range. Alternatively, three or more sensing electrodes may be provided in a sensor element. In such a case, a Au abundance ratio in each sensing electrode is determined appropriately, and further, output selection conditions for selecting a sensor output used to calculate a concentration are determined appropriately from the sensor output obtained for each sensing electrode. Consequently, a gas sensor having three or more levels of measurement concentration range per electrode can be achieved.

What is claimed is:

1. A mixed-potential gas sensor for measuring a concentration of a predetermined gas component of a measurement gas, said gas sensor comprising:
    a sensor element mainly made of an oxygen-ion conductive solid electrolyte;
    a plurality of sensing electrodes located on a surface of said sensor element, each of said plurality of sensing electrodes configured to sense said predetermined gas component; and
    at least one reference electrode including a cermet including Pt and an oxygen-ion conductive solid electrolyte,
    wherein
    said plurality of sensing electrodes each include a cermet including a noble metal and an oxygen-ion conductive solid electrolyte,
    said noble metal includes Pt and Au,
    a Au abundance ratio, which is an area ratio of a portion covered with said Au to a portion at which said Pt is exposed in a surface of noble metal particles forming each of said plurality of sensing electrodes, differs among said plurality of sensing electrodes, and
    said gas sensor determines a concentration of said predetermined gas component based on a potential difference between each of said plurality of sensing electrodes and said at least one reference electrode.

2. The gas sensor according to claim 1, wherein
    said plurality of sensing electrodes comprise a first sensing electrode and a second sensing electrode,
    said Au abundance ratio of said first sensing electrode is 0.7 or more,
    said Au abundance ratio of said second sensing electrode is 0.1 or more and less than 0.7, and
    said gas sensor determines the concentration of said predetermined gas component based on a first sensor output that is a potential difference between said first sensing electrode and said at least one reference electrode or a second sensor output that is a potential difference between said second sensing electrode and said at least one reference electrode.

3. The gas sensor according to claim 2, wherein
    said at least one reference electrode comprises a first reference electrode and a second reference electrode, and
    a potential difference between said first sensing electrode and said first reference electrode is said first sensor output, and a potential difference between said second sensing electrode and said second reference electrode is said second sensor output.

4. The gas sensor according to claim 2, wherein said first and second sensing electrodes are adjacent to each other in a longitudinal direction of said sensor element on one surface of said sensor element.

5. The gas sensor according to claim 2, wherein said first and second sensing electrodes are respectively located on two opposite surfaces of said sensor element.

6. The gas sensor according to claim 3, wherein said first and second sensing electrodes are adjacent to each other in a direction perpendicular to a longitudinal direction of said sensor element on one surface of said sensor element.

7. The gas sensor according to claim 2, wherein said gas sensor is configured to
    determine the concentration of said predetermined gas component based on said first sensor output when an emission source of said measurement gas is in a normal operation, and
    determine the concentration of said predetermined gas component based on said second sensor output when the emission source of said measurement gas emits said predetermined gas component at a concentration higher than a concentration in the normal operation.

8. The gas sensor according to claim 2, wherein said gas sensor is configured to
    determine the concentration of said predetermined gas component based on said first sensor output when an absolute value of a time differential value of said first sensor output is not smaller than an absolute value of a time differential value of said second sensor output, and
    determine the concentration of said predetermined gas component based on said second sensor output when the absolute value of the time differential value of said first sensor output is smaller than the absolute value of the time differential value of said second sensor output.

9. The gas sensor according to claim 2, wherein
    at least one of a first sensitivity characteristic and a second sensitivity characteristic is experimentally identified in advance, said first sensitivity characteristic representing a functional relationship between the concentration of said predetermined gas component and said first sensor output, said second sensitivity characteristic representing a functional relationship between the concentration of said predetermined gas component and said second sensor output,
    in a case where said first sensitivity characteristic has been identified, an upper limit value for said first sensor output in use of said first sensor output to calculate the concentration is set based on said first sensitivity characteristic,
    in a case where said second sensitivity characteristic has been identified, a lower limit value for said second sensor output in use of said second sensor output to calculate the concentration is set based on said second sensitivity characteristic, and
    said gas sensor is configured to
      calculate the concentration of said predetermined gas component based on said first sensor output and said first sensitivity characteristic when said first sensor output is not greater than said upper limit value, and calculate the concentration of said predetermined gas component based on said second sensor output and said second sensitivity characteristic when said first sensor output exceeds said upper limit value, or
      calculate the concentration of said predetermined gas component based on said second sensor output and said second sensitivity characteristic when said second sensor output is not smaller than said lower limit value, and calculate the concentration of said predetermined gas component based on said first sensor output and said first sensitivity characteristic when said second sensor output is smaller than said lower limit value.

10. The gas sensor according to claim 1, further comprising
at least one electrode protective layer that is a porous layer covering at least said plurality of sensing electrodes.

11. The gas sensor according to claim 1, wherein
said sensor element further includes a reference gas introduction space separate from a space containing said measurement gas, into which a reference gas is introduced, and
said at least one reference electrode is placed under an atmosphere of said reference gas.

12. The gas sensor according to claim 11, wherein
said sensor element further includes a reference gas introduction layer that is a porous layer in communication with said reference gas introduction space, and
said at least one reference electrode is covered with said reference gas introduction layer.

13. The gas sensor according to claim 11, wherein said at least one reference electrode is exposed to said reference gas introduction space.

14. The gas sensor according to claim 1, wherein said predetermined gas component comprises at least one of a hydrocarbon component or a carbon monoxide component.

15. The gas sensor according to claim 3, wherein said first and second sensing electrodes are adjacent to each other in a longitudinal direction of said sensor element on one surface of said sensor element.

16. The gas sensor according to claim 3, wherein said first and second sensing electrodes are respectively located on two opposite surfaces of said sensor element.

17. The gas sensor according to claim 3, wherein said gas sensor is configured to
determine the concentration of said predetermined gas component based on said first sensor output when an emission source of said measurement gas is in a normal operation, and
determine the concentration of said predetermined gas component based on said second sensor output when the emission source of said measurement gas emits said predetermined gas component at a concentration higher than a concentration in the normal operation.

18. The gas sensor according to claim 3, wherein said gas sensor is configured to
determine the concentration of said predetermined gas component based on said first sensor output when an absolute value of a time differential value of said first sensor output is not smaller than an absolute value of a time differential value of said second sensor output, and
determine the concentration of said predetermined gas component based on said second sensor output when the absolute value of the time differential value of said first sensor output is smaller than the absolute value of the time differential value of said second sensor output.

19. The gas sensor according to claim 3, wherein
at least one of a first sensitivity characteristic and a second sensitivity characteristic is experimentally identified in advance, said first sensitivity characteristic representing a functional relationship between the concentration of said predetermined gas component and said first sensor output, said second sensitivity characteristic representing a functional relationship between the concentration of said predetermined gas component and said second sensor output,
in a case where said first sensitivity characteristic has been identified, an upper limit value for said first sensor output in use of said first sensor output to calculate the concentration is set based on said first sensitivity characteristic,
in a case where said second sensitivity characteristic has been identified, a lower limit value for said second sensor output in use of said second sensor output to calculate the concentration is set based on said second sensitivity characteristic, and
said gas sensor is configured to
calculate the concentration of said predetermined gas component based on said first sensor output and said first sensitivity characteristic when said first sensor output is not greater than said upper limit value, and calculate the concentration of said predetermined gas component based on said second sensor output and said second sensitivity characteristic when said first sensor output exceeds said upper limit value, or
calculate the concentration of said predetermined gas component based on said second sensor output and said second sensitivity characteristic when said second sensor output is not smaller than said lower limit value, and calculate the concentration of said predetermined gas component based on said first sensor output and said first sensitivity characteristic when said second sensor output is smaller than said lower limit value.

20. The gas sensor according to claim 2, further comprising
at least one electrode protective layer that is a porous layer covering at least said plurality of sensing electrodes.

* * * * *